United States Patent
Kaneda et al.

(10) Patent No.: US 7,390,482 B2
(45) Date of Patent: Jun. 24, 2008

(54) DRUG FOR AUDITORY DYSFUNCTION

(75) Inventors: Yasufumi Kaneda, Minoh (JP); Kazuo Oshima, Minoh (JP); Ryuichi Morishita, Osaka (JP); Takeshi Kubo, Kobe (JP)

(73) Assignee: Anges MG, Inc., Ibaraki-shi, Osaka (JP)

( * ) Notice: Subject to any disclaimer, the term of this patent is extended or adjusted under 35 U.S.C. 154(b) by 391 days.

(21) Appl. No.: 10/527,195

(22) PCT Filed: Oct. 2, 2003

(86) PCT No.: PCT/JP03/12674

§ 371 (c)(1),
(2), (4) Date: Mar. 10, 2005

(87) PCT Pub. No.: WO2004/030702

PCT Pub. Date: Apr. 15, 2004

(65) Prior Publication Data

US 2006/0233755 A1   Oct. 19, 2006

(30) Foreign Application Priority Data

Oct. 2, 2002   (JP)   ............................. 2002-289639

(51) Int. Cl.
*A01N 63/00*   (2006.01)
*A01N 65/00*   (2006.01)
*A01N 43/04*   (2006.01)

(52) U.S. Cl. .................. 424/93.2; 424/93.1; 514/44

(58) Field of Classification Search ................ 424/93.2; 514/44
See application file for complete search history.

(56) References Cited

U.S. PATENT DOCUMENTS

| | | | |
|---|---|---|---|
| 6,017,886 A | 1/2000 | Carnahan | |
| 6,136,785 A | 10/2000 | Corwin et al. | |
| 2001/0039048 A1* | 11/2001 | Wu et al. | ................... 435/325 |
| 2003/0176347 A1 | 9/2003 | Nakamura et al. | |

FOREIGN PATENT DOCUMENTS

| | | | |
|---|---|---|---|
| AU | 199929281 B2 | | 9/1999 |
| CN | 1358543 A | * | 7/2002 |
| EP | 0847757 A1 | | 6/1998 |
| EP | 1136083 A1 | | 9/2001 |
| EP | 1142590 A1 | | 10/2001 |
| JP | 2002-503687 | | 2/2002 |
| WO | 97/07824 | | 3/1997 |
| WO | 97/30722 | | 8/1997 |
| WO | 98/00014 | | 1/1998 |
| WO | 98/19700 | | 5/1998 |
| WO | 99/06064 | | 2/1999 |
| WO | 99/42088 | | 8/1999 |
| WO | 00/55195 | | 9/2000 |
| WO | 02/22162 A1 | | 3/2002 |

OTHER PUBLICATIONS

Kinoshita et al. (1992) Jikken Igaku 10(3):330-339 and summary in English.
Maina et al. (1997) "Met receptor signaling is required for sensory nerve development and HGF promotes axonal growth and survival of sensory neurons" Genes & Dev. 11:3341-3350 (1997).
Wada et al. (1998) Audiology Japan 41(5):355-356 and summary in English.
Fisher "Genes and protein in renal development" Exp. Nephrol. 10:102-113 (2002) abstract only.
Korhonen et al. "Expression of c-Met in developing rat hippocampus: Evidence for HGF as a neurotrophic factor for calbindin D-expressing neurons" Eur. J. Neurosci. 12:3453-3461 (2000).

* cited by examiner

*Primary Examiner*—Michael C. Wilson
(74) *Attorney, Agent, or Firm*—Nixon & Vanderhye P.C.

(57) ABSTRACT

The present invention provides a pharmaceutical preparation for hearing impairment, which is suitable for gene therapy of hearing impairment, that is, a pharmaceutical preparation for hearing impairment which comprises a virus envelope vector encapsulating a hepatocyte growth factor (HGF) gene or its plasmid as an active ingredient. Particularly, it is suitable as a pharmaceutical preparation for gene therapy for the purpose of prevention and treatment of deafness.

2 Claims, 3 Drawing Sheets a b c

DRUG FOR AUDITORY DYSFUNCTION

This application is the U.S. national phase of international application PCT/JP2003/012674 filed 2 Oct. 2003 which designated the U.S. and claims benefit of JP 2002-289639, dated 2 Oct. 2002, the entire content of which is hereby incorporated by reference.

TECHNICAL FIELD

The present invention relates to a pharmaceutical preparation for hearing impairment, which is preferable as an agent for preventing, treating or ameliorating hearing impairment such as deafness, used in gene therapy etc.

BACKGROUND ART

Hearing impairment is the most prevalent sensory deficit of human beings, and are said to occur in at least one of ten persons. Hearing impairment can be caused by a variety of factors including ototoxic substances such as aminoglicoside antibiotics or cisplatin (CDDP), noise and ageing.

These factors affect the inner ear hair cells in the organ of Corti which function as sensory cells that collect and transfer auditory signals to the brain via the auditory neurons. Moreover, degeneration of the auditory nerve occurs secondary to the loss of the sensory hair cells, thus exacerbating the functional impairment of hearing.

In general, hair cells and auditory neurons in mammalian vertebrates have no capacity for postembryonic cellular mitosis to generate new hair cells and neurons. In the mammalian stato-acoustic epithelia, a low level of regeneration is possible for the vestibular receptors in vivo. However, no regeneration of auditory sensory epithelium was observed in vivo, except a very restricted regeneration observed in neonatal mouse cochlear in vitro.

For the treatment of severely deaf ears, the cochlear implant has provided great benefits to patients and has been shown to provide an effective intervention. However, the benefit of cochlear prosthesis depends on the quality and quantity of the auditory nerve population, and their loss severely compromises the hearing benefits it provides.

The past studies show a clear relationship between the total number of viable auditory neurons available for stimulation and the performance of subjects receiving cochlear implants. This shows that the implant cannot always produce satisfactory results.

It is therefore necessary to develop the therapeutic strategy of preserving or regenerating the auditory neurons to increase the effectiveness of the implant. Recent studies revealed that multiple neurotrophic factors such as nerve growth factor (NGF), glial cell line-derived neurotrophic factor (GDNF), brain-derived neurotrophic factor (BDNF), neurotrophic factor-3 or NT-4/5 have been shown to have effects on the survival of inner ear auditory neurons, including spiral ganglion cells (SGCs).

A prior art relevant to the present invention, that is, U.S. Pat. No. 6,136,785 discloses a method of protecting sensory hair cells in the inner ear against damage caused by ototoxic substances such as aminoglicoside, which comprises administering a growth factor or a mixture thereof into a vertebrate. As its relevant prior arts, WO-A 98/00014, U.S. Pat. No. 6,017,886, JP-A 2002-503687 etc. are also known.

DISCLOSURE OF THE INVENTION

The object of the present invention is to provide a pharmaceutical preparation for hearing impairment, which can prevent or treat hearing impairment by preserving or regenerating the auditory neurons.

The present inventors focused attention on the fact that a hepatocyte growth factor (HGF) gene is a therapeutic substance effective for curing hearing impairment, and they conducted extensive study to complete the present invention.

As a means for solving the problem, the invention in claim 1 provides a pharmaceutical preparation for hearing impairment, which comprises a hepatocyte growth factor (HGF) gene as an active ingredient.

As another means for solving the problem, the invention in claim 2 provides a pharmaceutical preparation for hearing impairment, which comprises a plasmid of a hepatocyte growth factor (HGF) gene as an active ingredient.

As another means for solving the problem, the invention in claim 3 provides a pharmaceutical preparation for hearing impairment, which comprises a virus envelope vector encapsulating a hepatocyte growth factor (HGF) gene or its plasmid as an active ingredient.

As another means for solving the problem, the invention in claim 4 provides the pharmaceutical preparation for hearing impairment according to claim 3, wherein the virus is one member selected from the group consisting of Sendai virus, retrovirus, adenovirus, adeno-associated virus, herpes virus, vaccinia virus, pox virus and influenza virus.

The pharmaceutical preparation for hearing impairment according to the present invention is suitable as an agent for preventing hearing impairment or as an agent for treating or ameliorating hearing impairment, and is particularly suitable as a pharmaceutical preparation for genetic therapy for deafness.

The present invention provides use of a hepatocyte growth factor (HGF) gene or a plasmid of a hepatocyte growth factor (HGF) gene for producing a pharmaceutical preparation for hearing impairment, as well as a method of treating hearing impairment, which comprises administering, to a patient with hearing impairment, a hepatocyte growth factor (HGF) gene or a plasmid of a hepatocyte growth factor (HGF) gene in an amount effective for the treatment.

As used herein, the "hepatocyte growth factor (HGF)" is a physiologically active peptide exhibiting various pharmacological actions, represented by SEQ ID NO:1 in the Sequence Listing, and the pharmacological actions are described in, for example, "Jikken Igaku" (Experimental Medicine), Vol. 10, No. 3 (extra issue) 330-339(1992), and WO-A97/7824 describes various applications thereof as the prior art, but no pharmacological action thereof on hearing impairment is known.

DETAILED DESCRIPTION OF THE INVENTION

The hepatocyte growth factor (HGF) gene contained as an active ingredient in the pharmaceutical preparation for hearing impairment according to the present invention refers to a gene capable of expressing HGF, and is specifically represented by SEQ ID NO: 2 in the Sequence List. This gene also encompasses genes consisting of the same gene sequence as above except that the sequence is partially deleted or substituted by other base(s), has another nucleotide sequence inserted into it, or has a base added to the 5'- and/or 3'-end thereof insofar as their expressed polypeptides have substantially the same effect as that of HGF.

As the HGF gene, an HGF gene described in Nature 342, 440 (1989), JP-A 5-111383, WO-A 90/10651, Biochem. Biophys. Res. Commun. 163, 967 (1989) etc. may be used.

The HGF gene can be used in a suitable vector, preferably in a form incorporated in a plasmid.

The HGF gene encapsulating in a virus envelope from which RNA was removed, or a virus envelope vector encapsulating a plasmid containing the HGF gene, can be used as the HGF gene.

The virus used herein may be wild-type virus or recombinant virus. This virus is preferably one member selected from the group consisting of Sendai virus, retrovirus, adenovirus, adeno-associated virus, herpes virus, vaccinia virus, pox virus and influenza virus. Among these viruses, HVJ is more preferable, and particularly inactivated HVJ is preferable. The term "inactivated" means that the genome of the virus is inactivated.

Specifically, Sendai virus for example VR-105, VR-907 etc. can be purchased from American Type Culture Collection (ATCC), telephone 1-703-365-2700, P.O. Box 1549, Manassas, Va. 20108, USA.

http://www.atcc.org/SearchCatalogs/longview.cfm?view=a v,152376,VR-105&text=Sendai&max=20 http://www.atcc.org/SearchCatalogs/longview.cfm?view=a v,1375478,VR-907&text=Sendai&max=20

As the virus envelope vector, an HVJ envelope vector disclosed in WO-A 01/57204 can be used.

The form of the pharmaceutical preparation for hearing impairment according to the present invention is determined in relationship with the administration method, but in the present invention, the pharmaceutical preparation is formed preferably into an injection.

When the pharmaceutical preparation for hearing impairment according to the present invention is formed into an injection, the injection can be produced by mixing the HGF gene, a plasmid of the HGF gene, or a virus envelope vector encapsulating the hepatocyte growth factor (HGF) gene or the plasmid, with a pharmaceutically acceptable carrier (sterilized water, physiological saline, phosphate buffered physiological saline, a buffer solution, etc.).

If necessary, the carrier can contain a very small amount of additives such as substances enhancing isotonicity and chemical stability. Such substances are used in such an amount and concentration as not to be toxic to the patient.

Such substances include buffering agents such as phosphoric acid, citric acid, succinic acid, acetic acid and other organic acids or salts thereof; antioxidants such as ascorbic acid; polypeptides with a low-molecular weight (less than about 10 residues) (for example, polyarginine or tripeptide); protein (for example, serum albumin, gelatin, immunoglobulin); hydrophilic polymers (for example, polyvinyl pyrrolidone); amino acid (for example, glycine, glutamic acid, aspartic acid, arginine); monosaccharide, disaccharide and other hydrocarbons (for example, glucose, mannose, sucrose, dextrin, cellulose or its derivatives); chelating agents (for example, EDTA); sugar alcohol (for example, mannitol, sorbitol); counter ion (for example, sodium); nonionic surfactants (for example, polysorbate, poloxamer); polyethylene glycol etc.

When the pharmaceutical preparation for hearing impairment according to the present invention is formed into an injection, the pharmaceutical preparation is stored as a dried product and a diluent respectively, or as an aqueous solution, in a sealed ampoule and vial.

When the pharmaceutical preparation for hearing impairment according to the present invention is administered in the form of e.g. an injection into humans, it is possible to employ a method of direct administration into the inner ear via a cochlea, a method of direct administration into the inner ear via a semicircular duct, a method of administering it into cerebrospinal fluid to carry it to the inner ear, a method of administering it into the middle ear to infiltrate the inner ear, a method of directly administering it into the inner ear by a device for sticking or gradually releasing it to an inserted electrode, which was integrated in the inner ear upon surgery for implanting the cochlear implant.

The pharmaceutical preparation for hearing impairment according to the present invention is formulated and administered in consideration of the clinical conditions of each patient (for example, conditions to be prevented or treated), the administration method, administration site, administration schedule and other factors known by those skilled in the art, in a mode in accordance with medical implementation standards. Accordingly, the effective amount and suitable administration amount of the pharmaceutical preparation for hearing impairment according to the present invention are determined with such items taken into consideration.

When the pharmaceutical preparation for hearing impairment according to the present invention is administered in the form of a virus envelope vector, the amount of the virus envelope vector administered is usually 0.001 μg to 1 g, preferably 0.01 μg to 500 mg, more preferably 0.1 μg to 100 mg, per kg of patient' body weight.

The amount of the HGF gene in the virus envelope vector administered is usually 0.01 μg to 500 mg, preferably 0.1 μg to 10 mg, more preferably 1 μg to 1 mg, per kg of patient' body weight.

The pharmaceutical preparation for hearing impairment according to the present invention can be used as a medicine for gene therapy of hearing impairment, is suitable as an agent for preventing, treating or ameliorating hearing impairment, and is suitable as an agent for preventing, treating or ameliorating hearing impairment, particularly deafness.

The present inventors revealed in their study that the injection of HVJ-E encapsulating human HGF into subarachnoid cerebrospinal fluid prevented loss of hair cells and spiral ganglion cells by apotosis inhibition.

That is, administration of the HGF gene just before treatment with kanamycin can prevent hearing impairment, and can recover auditory functions even after induction of hearing impairment with kanamycin.

These results indicate the significantly outstanding usefulness of HGF gene therapy using the HVJ-E vector.

For transfection of the gene into the inner ear, the following surgical techniques are fundamentally practiced.

i) Direct injection into the cochlea by resection of the cochlea.

ii) Administration via a round window membrane by injection through the membrane or by permeation with a gel containing the vector placed on the intact membrane.

iii) Administration into the inner ear through a posterior semicircular duct by resection.

iv) Administration into an endolymphatic sac.

Up to now, some virus vectors such as adenovirus vector, herpes virus vector and adeno-associated vector have been administered directly into the inner ear by using any one of the 4 techniques described above.

However, the respective techniques have advantages and disadvantages from the viewpoint of invasive property and effectiveness.

In this study, the present inventors injected the HVJ-E vector into subarachnoid cerebrospinal fluid in order to prevent invasion of the inner ear by direct injection into the cochlea.

By this method, the expression of the introduced gene in the cerebrospinal fluid was confirmed by enzyme activity and immune staining, and no significant damage in the brain or ear tissues was recognized. This fact suggests that after administration into the cerebrospinal fluid, the HVJ-E vector itself reaches spiral ganglion cells in the inner ear, thus indicating some possible pathways from the subarachnoid cerebrospinal fluid into the inner ear.

When the vector was injected into the membrane, no luciferase activity was observed in separate organs, and thus the most possible pathway for the vector to reach from the subarachnoid cerebrospinal fluid to the inner ear is considered to be via a cochlear duct.

If the vector spread via blood stream into the whole body, luciferase activity after intravenous injection would be recognized first in the spleen, and thus expression of the introduced gene should be detected in separate organs such as spleen and lung.

Conventionally, neutrophic factors such as NGF, BDNF, GDNF and NT-3 have been used in treatment of the sense of hearing.

However, HGF has not been used for this purpose. It has been revealed that HGF shows not only an effect on the liver but also neutrophic activity in hippocampus, cerebral cortex, sensory neurons, motor neurons etc., and this time, the present inventors indicated that human HGF was recognized in both subarachnoid cerebrospinal fluid and spiral ganglion cells, and that the human HGF induced endogenous HGF in rats.

HGF gene therapy in the auditory system is considered to have some advantages over conventional gene therapy utilizing neutrophin.

Further, combined use of an artificial inner ear and HGF gene therapy, that is, the administration of HGF gene during artificial inner ear surgery, would also be effective.

Hearing impairment are accompanied by a loss in hair cells and spiral ganglion cells, and prevention of this loss in the cells is worked out by the protective action of HGF against cell death by apotosis. Expression of HGF is effective in recovery of functions even after induction of hearing impairment by treatment with kanamycin.

Thus, HGF gene therapy is one highly promising method for treatment of hearing impairment in the sensory nerve.

This study provides a new finding and technique for treatment of hearing impairment by a combination of HGF gene and HVJ-E vector transfer system.

The pharmaceutical preparation for hearing impairment according to the present invention is suitable as a pharmaceutical preparation for gene therapy particularly for purposes such as prophylaxis, therapy etc. of deafness.

EXAMPLES

Figure 1:
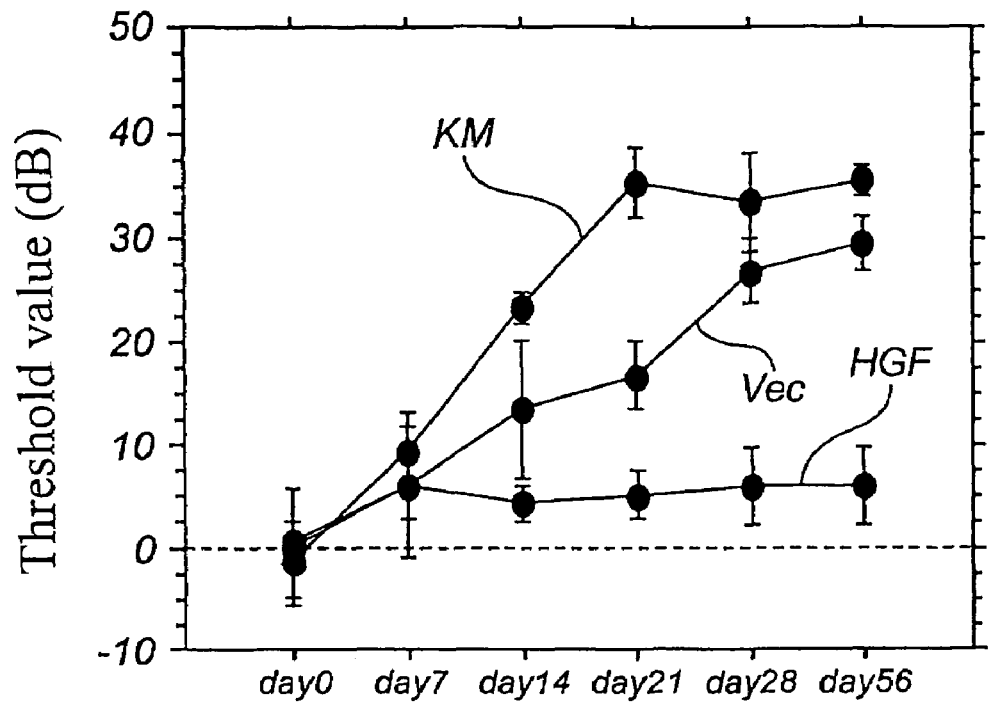
FIG. 1 is a graph showing a change with day in auditory functions in an auditory function test in Examples.

Hereinafter, the present invention is described in more detail by reference to Examples, but the present invention is not limited by Examples.

Preparation of Plasmid DNA pCMV-lacZ (9.2 kb) was constructed by inserting a HindIII-BamHI fragment of pSV-β-galactosidase (Promega Corp., Madison, Wis., USA) into pcDNA3 (5.4 kb) (Invitrogen, San Diego, Calif., USA) at the HindIII and BamHI sites.

pCMV-luciferase-GL3 (pcLuc-GL3: 7.4 kb) was constructed by cloning the luciferase gene from the pGL3-basic Vector (Promega) into pcDNA3(Invitrogen).

pVAX1-hHGF (5.2 kb) was constructed by inserting the human HGF cDNA into pVAX1 (3.0 kb) (Invitrogen) at the BamHI and NotI sites.

Plasmids were purified with the QIAGEN plasmid isolation kit (Qiagen, Hilden, Germany).

Preparation of HVJ-Envelope Vector

Hemagglutinating virus of Japan (HVJ; Sendai virus) envelope vector (HVJ-E) was constructed by encapsulating plasmid DNA into inactivated HVJ particles according to Example 8 in WO-A 01/27204, except that HVJ was purified by centrifugation and inactivated by irradiation with UV rays.

Preparation of HVJ-E Suspension (Pharmaceutical Preparation for Hearing Impairment According to the Present Invention)

UV-inactivated HVJ (Z strain), 10000 hemmaglutinating unit, was mixed with 200 µg of plasmid DNA and 0.3% Triton X, washed with balanced salt solution (BSS: 137 mM NaCl, 5.4 mM KCl, 10 mM Tris-HCl, pH 7.6), and adjusted in 100 µl with BSS for intrathecal infusion. HVJ-E encapsulating pCMV-lacZ, pcLuc-GL3, pVAX1-hHGF, pcDNA3 or pVAX1 plasmid DNA was used in the present examples.

Experimental Animals and Treatment Groups

Sprague-Dawley male rats (6 weeks of age; 200-210 g) with normal Preyer's reflex were obtained from Charles River Japan (Atsugi, Japan). All procedures were conducted in accordance with the guidelines of the Animal Committee of Osaka University.

Animals were divided into five groups: the protection group, the rescue group, the protection/rescue group, the vector-control group and the no-therapy group. Animals of all groups were bilaterally deafened by aminoglycoside intoxication; kanamycin sulfate (Meiji Seika, Tokyo, Japan) was administered daily by subcutaneous injection (400 mg/kg/day) for 14 consecutive days.

The protection group and the protection/rescue group were intrathecally injected with HVJ-E suspension encapsulating hHGF gene (pVAX1-hHGF) on the first day of the kanamycin treatment.

The vector-control group was administered with HVJ-E suspension encapsulating the control vector (pVAX1) by intrathecal injection in the same way as above.

On the last day of the kanamycin treatment (on the 14th day), the rescue group and the protection/rescue group were injected with HVJ-E encapsulating pVAX1-hHGF.

In addition, HVJ-E encapsulating pCMV-lacZ or pcLuc-GL3 was administered to animals for histochemical analyses and luciferase assays.

After this procedure, expression of β-galactosidase was observed 7 days after transfection and luciferase activity was measured 1 day after transfection.

In Vivo Gene Transfer to Subarachnoid Space

In this study, gene transfer into the cisterna magna using infusion of HVJ-E was employed as in vivo gene transfer into the CNS and the inner ear.

For infusion into the subarachnoid space, after animals were anaesthetized with ketamine (Sankyo, Japan) and xylazin (Bayer), the head of each animal was fixed in the prone position, and the atlanto-occipital membrane was exposed through an occipitocerebral midline incision.

A stainless cannula (27 gauge; Beckton Dikinson) was introduced into cisterna magna (subarachnoid space). After the withdrawal of the cerebrospinal fluid (100 μl) for confirmation of the cannula position and to avoid increased intracerebral pressure, HVJ-E (100 μl) encapsulating marker gene, hHGF gene or control vector was infused at the speed of 50 μl/min.

Afterwards, the animals were placed head down for 30 minutes. All rats showed no weight loss, loss of activity or behavioral change after administration.

Assay for Luciferase Activity

Rats transfected with luciferase gene were sacrificed under anesthesia 24 hours after transfection. Organs (brain, lung, spleen, liver and cochlear) were harvested and placed individually in FALCON 50 ml tubes.

Luciferase activity was measured with a luciferase assay kit (Promega) as described previously (44 of HVJ-E). Luciferase levels were normalized by determining the protein concentrations of the tissue extracts (44 of HVJ-E). Luciferase units were expressed as relative light units (RLU) per gram of tissue protein.

Enzyme Immunoassay for Human HGF in Cerebrospinal Fluid

Cerebrospinal fluid (CSF) (100 μL) from the rats, 5 and 14 days after the injection of HVJ-E encapsulating hHGF gene, was used for the experiments.

The concentration of human HGF and rat HGF in the CSF was determined by enzyme-immunoassay using anti-human and anti-rat HGF antibody according to the manufacturer's manual (Institute of Immunology, Tokyo, Japan).

The antibody against human HGF reacted with only human HGF and not with rat HGF. The antibody against rat HGF reacted with both human and rat HGF.

Reverse Transcription Polymerase Chain Reaction

Rats were deeply anesthetized with ether, decapitated, and the temporal bones were placed in cold RNase-free saline. The otic capsule was removed, and whole cochlears were isolated under the dissection microscope. Tissues from the rats were pooled in lysis buffer, homogenized using a homogenizer, and total RNA was isolated using RNeasy Mini Kit (Qiagen). RNA was reverse-transcribed with the SuperScript First-strand Synthesis System for RT-PCR (Invitrogen).

First-strand cDNA was amplified using the specific primers for human HGF and GAPDH: HGF, upstream primer 5'-TTCACAAGCAATCCAGAGGTACGC-3', downstream primer 5'-GAGGGTCAAGAGTATAGCACCATG-3'; GAPDH, upstream primer
5'-TGAAGGTCGGAGTCAACGGA-3', downstream primer
5'-GATGGCATGGACTGTGGTCA-3' (which are SEQ ID NOS: 3, 4, 5 and 6 respectively in the Sequence List).

The PCR conditions were optimized for each set of primers. The PCR reaction mixture contained 5 μl of cDNA, 5 μl of 10×PCR buffer, 4 μl of 2.5 mM dNTP, 2.5 μl of 20 pM upper and lower primers, and 1.5U of Taq polymerase, distilled water added to 45 μl.

Thermocycling conditions: HGF, 94° C. for 45 s, 70° C. for 2 min and 72° C. for 2 min; GAPDH, 94° C. for 45 s, 58° C. for 1 min and 72° C. for 2 min.

Evaluation of the Auditory Function

To evaluate the physiological condition of auditory function, we performed auditory brainstem response (ABR) audiometry.

The ABRs were measured one day prior to the first day of the kanamycin administration to determine the baselines and were again recorded 7, 14, 21, 28 and 56 days from the beginning of the kanamycin treatment.

Prior to each test of auditory function, the animals were anesthetized with an intramuscular injection of a ketamine (50 mg/kg)-xylazine (10 mg/kg) solution. Needle electrodes were placed subcutaneously at the ipsilateral right pinna (reference electrode), the contralateral pinna (ground electrode) and at the vertex (active electrode). All recordings were performed in a sound-proof room with a Nihon-Kohden Neuropack IV (MEM-4104) system.

The potentials were evoked by single-wave 100 μs click sounds (10/s), and these monaural stimuli were delivered to the right ear by loudspeaker. Responses were digitally filtered (bandpass: 50-3000 Hz), amplified and averaged (500 responses).

The auditory threshold and the latency of P1 waves were assessed and calculated by comparison with each pre-study value. The intensity of the stimulus was varied in 2-dB stepwise increments to determine the threshold. Threshold is defined as the lowest intensity level at which responses could still be recorded in two consecutive trials to confirm response reproductivity. The results are shown in FIGS. 1 and 2.

Figure 2:
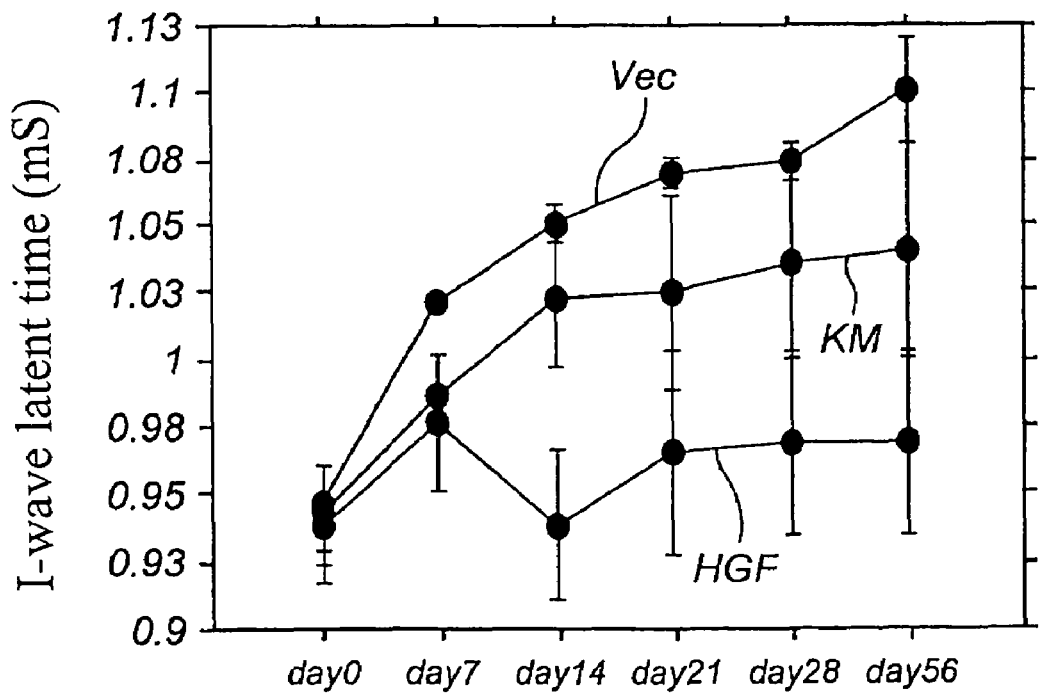
FIG. 2 is a graph showing a change with day in auditory functions in an auditory function test in Examples.

FIG. 1 shows threshold value (dB) from Day 0 to Day 56, and FIG. 2 shows I-wave latent time (mS). In the graph, HGF shows the protection group, the protection/rescue group, and the rescue group, Vec in the graph shows the vector-control group, and KM in the graph shows the non-therapy group.

As is evident from FIGS. 1 and 2, the change in the sense of hearing (change in threshold value and I-wave latent time) of the protection group, the protection/rescue group, and the rescue group was slight even after 56 days, while the change in the sense of hearing (change in threshold value and I-wave latent time) of the vector-control group and the non-therapy group was significant.

Figure 3:
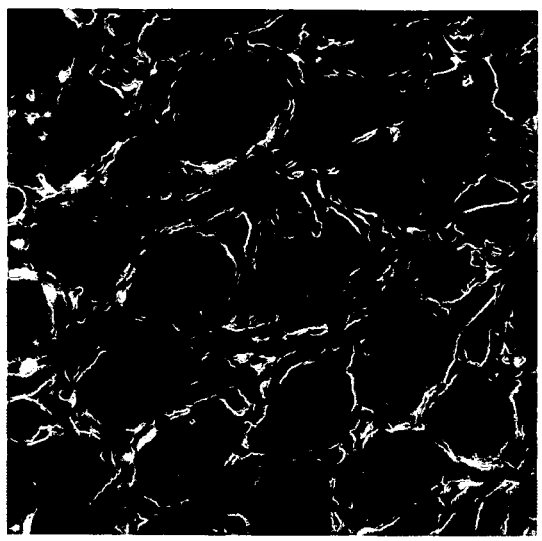
FIG. 3a is a microphotograph of intact spiral ganglion cells.
FIG. 3b is a microphotograph of a group treated with kanamycin.
FIG. 3c is a microphotograph of a group treated with kanamycin+HGF.
Figure 3:
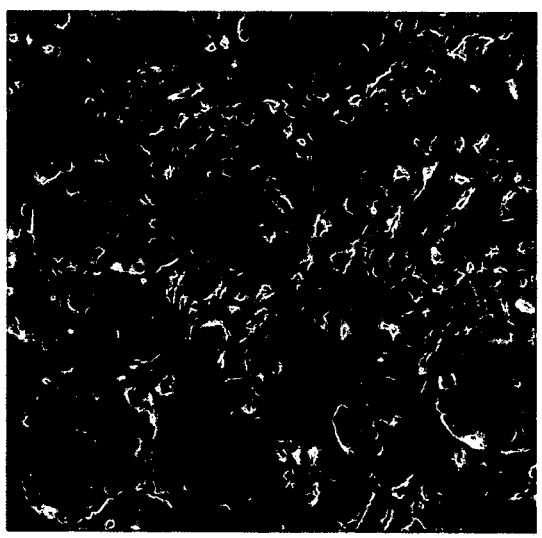
Figure 3:
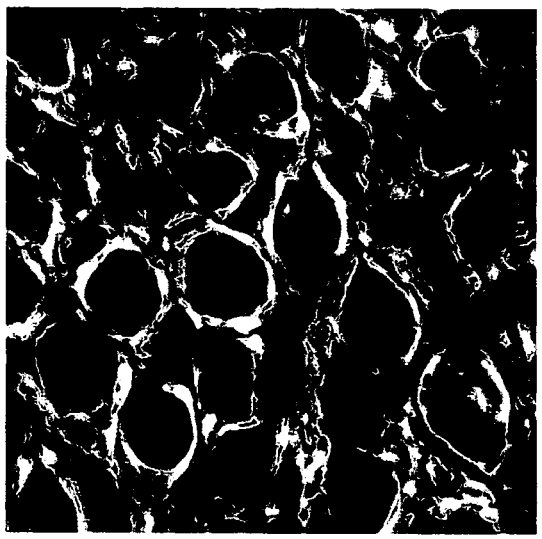

FIG. 3 shows optical microphotographs of spiral ganglion cell (SGC) of the cochlea (spiral tact): FIG. 3a shows that of the intact cochlea; FIG. 3b shows that of the group treated with kanamycin (non-therapy group); and FIG. 3c is that of the group treated with kanamycin+HGF (the protection group, the protection/rescue group and the rescue group).

As is evident from FIG. 3a to FIG. 3c, the spiral ganglion cells in the kanamycin+HGF treatment group was more intact than in the kanamycin treatment group.

Figure 4:
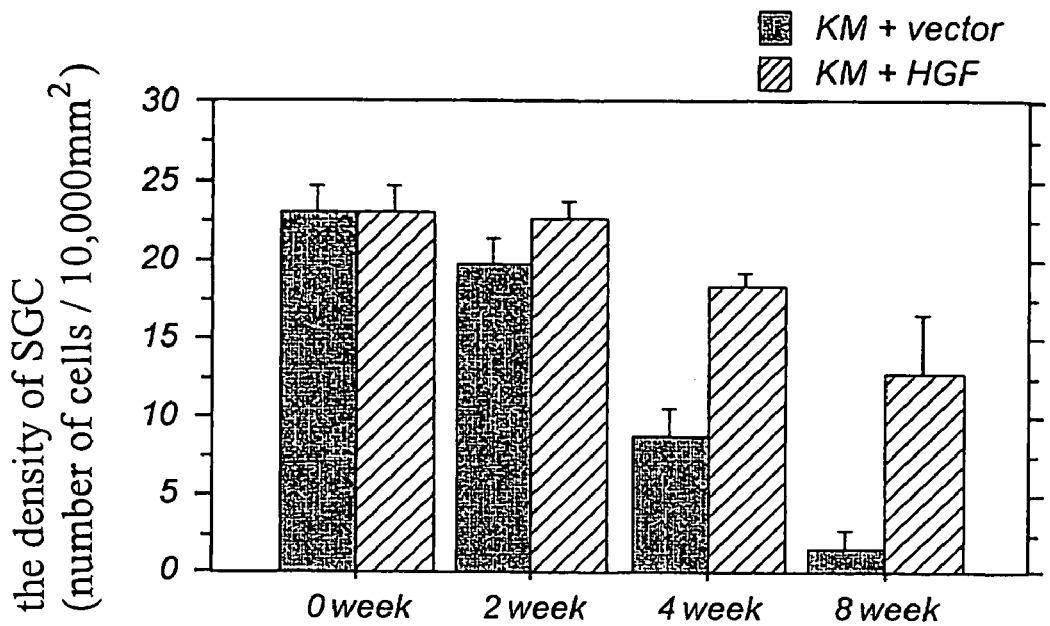
FIG. 4 is a graph showing the density of spiral ganglion cells in a group treated with kanamycin+HGF and in a group treated with kanamycin+vector.

FIG. 4 shows the density of spiral ganglion cells (number of cells/10,000 mm$^2$) in the group treated with kanamycin+

HGF (the protection group, the protection/rescue group and the rescue group) and in the group treated with kanamycin+ vector (vector-control group).

Figure 5:
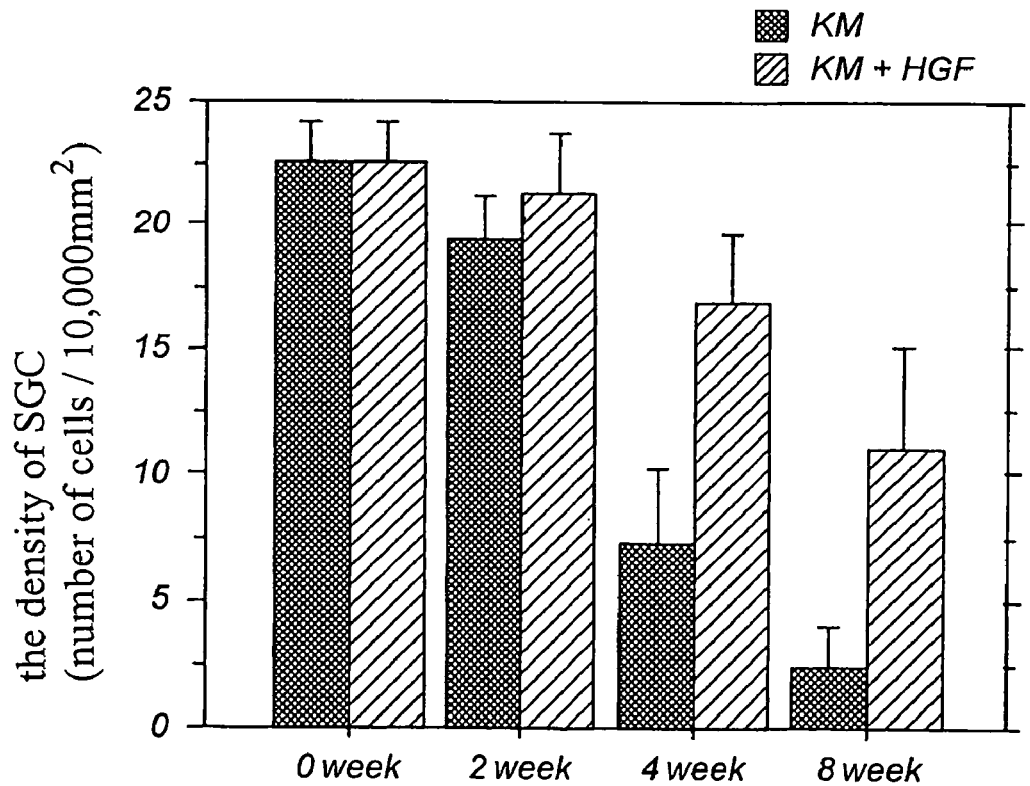
FIG. 5 is a graph showing the density of spiral ganglion cells in a group treated with kanamycin+HGF and in a group treated with kanamycin.

FIG. 5 shows the density of spiral ganglion cells (number of cells/10,000 mm$^2$) in the group treated with kanamycin+ HGF (the protection group, the protection/rescue group and the rescue group) and in the group treated with kanamycin (non-therapy group).

As is evident from FIGS. 4 and 5, the density of spiral ganglion cells was higher in the kanamycin+HGF treatment group than in the other treatment groups.

The above results are estimated due to preserve or regeneration of auditory neurons by administration of the HVJ-E suspension.

The invention claimed is:

1. A method of treating hearing impairment, which comprises intrathecally administering a plasmid encoding hepatocyte growth factor (HGF) encapsulated in an inactivated hemagglutinating virus of Japan (HVJ) particle to a patient with hearing impairment.

2. The method according to claim 1, wherein the hearing impairment is deafness.

* * * * *

SEQUENCE LISTING

<160> NUMBER OF SEQ ID NOS: 6

<210> SEQ ID NO 1
<211> LENGTH: 728
<212> TYPE: PRT
<213> ORGANISM: Homo sapiens

<400> SEQUENCE: 1

```
Met Trp Val Thr Lys Leu Leu Pro Ala Leu Leu Leu Gln His Val Leu
  1               5                  10                  15

Leu His Leu Leu Leu Leu Pro Ile Ala Ile Pro Tyr Ala Glu Gly Gln
             20                  25                  30

Arg Lys Arg Arg Asn Thr Ile His Glu Phe Lys Lys Ser Ala Lys Thr
         35                  40                  45

Thr Leu Ile Lys Ile Asp Pro Ala Leu Lys Ile Lys Thr Lys Lys Val
     50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300
```

```
Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
            325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
            405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
            435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720
```

Leu Thr Tyr Lys Val Pro Gln Ser
            725

<210> SEQ ID NO 2
<211> LENGTH: 2187
<212> TYPE: DNA
<213> ORGANISM: Homo sapiens

<400> SEQUENCE: 2

| | | | | |
|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | atcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgttttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| agcttttttgc | cttcgagcta | tcggggtaaa | gacctacagg | aaaactactg | tcgaaatcct | 540 |
| cgagggggaag | aaggggggacc | ctggtgtttc | acaagcaatc | cagaggtacg | ctacgaagtc | 600 |
| tgtgacattc | ctcagtgttc | agaagttgaa | tgcatgacct | gcaatgggga | gagttatcga | 660 |
| ggtctcatgg | atcatacaga | atcaggcaag | atttgtcagc | gctgggatca | tcagacacca | 720 |
| caccggcaca | aattcttgcc | tgaaagatat | cccgacaagg | gctttgatga | taattattgc | 780 |
| cgcaatcccg | atggccagcc | gaggccatgg | tgctatactc | ttgaccctca | cacccgctgg | 840 |
| gagtactgtg | caattaaaac | atgcgctgac | aatactatga | atgacactga | tgttcctttg | 900 |
| gaaacaactg | aatgcatcca | aggtcaagga | gaaggctaca | ggggcactgt | caataccatt | 960 |
| tggaatggaa | ttccatgtca | gcgttgggat | tctcagtatc | ctcacgagca | tgacatgact | 1020 |
| cctgaaaatt | tcaagtgcaa | ggacctacga | gaaaattact | gccgaaatcc | agatgggtct | 1080 |
| gaatcaccct | ggtgttttac | cactgatcca | aacatccgag | ttggctactg | ctcccaaatt | 1140 |
| ccaaactgtg | atatgtcaca | tggacaagat | tgttatcgtg | gaatggcaa | aaattatatg | 1200 |
| ggcaacttat | cccaaacaag | atctggacta | acatgttcaa | tgtgggacaa | gaacatggaa | 1260 |
| gacttacatc | gtcatatctt | ctgggaacca | gatgcaagta | agctgaatga | aattactgc | 1320 |
| cgaaatccag | atgatgatgc | tcatggaccc | tggtgctaca | cgggaaatcc | actcattcct | 1380 |
| tgggattatt | gccctatttc | tcgttgtgaa | ggtgatacca | cacctacaat | agtcaattta | 1440 |
| gaccatcccg | taatatcttg | tgccaaaacg | aaacaattgc | gagttgtaaa | tgggattcca | 1500 |
| acacgaacaa | acataggatg | gatggttagt | ttgagataca | gaaataaaca | tatctgcgga | 1560 |
| ggatcattga | taaaggagag | ttgggttctt | actgcacgac | agtgtttccc | ttctcgagac | 1620 |
| ttgaaagatt | atgaagcttg | gcttggaatt | catgatgtcc | acggaagagg | agatgagaaa | 1680 |
| tgcaaacagg | ttctcaatgt | tcccagctg | gtatatggcc | ctgaaggatc | agatctggtt | 1740 |
| ttaatgaagc | ttgccaggcc | tgctgtcctg | gatgattttg | ttagtacgat | tgatttacct | 1800 |
| aattatggat | gcacaattcc | tgaaaagacc | agttgcagtg | tttatggctg | gggctacact | 1860 |
| ggattgatca | actatgatgg | cctattacga | gtggcacatc | tctatataat | gggaaatgag | 1920 |
| aaatgcagcc | agcatcatcg | agggaaggtg | actctgaatg | agtctgaaat | atgtgctggg | 1980 |
| gctgaaaaga | ttggatcagg | accatgtgag | ggggattatg | gtggcccact | tgtttgtgag | 2040 |

-continued

```
caacataaaa tgagaatggt tcttggtgtc attgttcctg gtcgtggatg tgccattcca    2100
aatcgtcctg gtatttttgt ccgagtagca tattatgcaa aatggataca caaaattatt    2160
ttaacatata aggtaccaca gtcatag                                         2187
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

```
ttcacaagca atccagaggt acgc                                              24
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 4

```
gagggtcaag agtatagcac catg                                              24
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5

```
tgaaggtcgg agtcaacgga                                                   20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
gatggcatgg actgtggtca                                                   20
```